United States Patent [19]

Kaiser et al.

[11] Patent Number: 5,420,302

[45] Date of Patent: May 30, 1995

[54] PREPARATION OF CALCIUM L-ASCORBATE 2-PHOSPHATE

[75] Inventors: Klaus Kaiser, Neustadt; Friedhelm Balkenhohl, Limburgerhof; Joachim Paust, Neuhofen, all of Germany

[73] Assignee: BASF Aktiengesellschaft, Ludwigshafen, Germany

[21] Appl. No.: 102,745

[22] Filed: Aug. 6, 1993

[30] Foreign Application Priority Data

Aug. 12, 1992 [DE] Germany .................. 42 26 625.4

[51] Int. Cl.$^6$ .............................................. C07F 9/06
[52] U.S. Cl. ...................................................... 549/222
[58] Field of Search ........................................ 549/222

[56] References Cited

U.S. PATENT DOCUMENTS

| | | | |
|---|---|---|---|
| 4,999,437 | 3/1991 | Dobler et al. | 549/222 |
| 5,110,950 | 5/1992 | Seib et al. | 549/222 |
| 5,149,829 | 9/1992 | Seib et al. | 549/222 |
| 5,210,220 | 5/1993 | Pauling et al. | 549/222 |

FOREIGN PATENT DOCUMENTS

| | | |
|---|---|---|
| 388869 | 9/1990 | European Pat. Off. . |
| 1489249 | 6/1967 | France . |

*Primary Examiner*—C. Warren Ivy
*Assistant Examiner*—Raymond Covington
*Attorney, Agent, or Firm*—Keil & Weinkauf

[57] ABSTRACT

A process for isolating the calcium salt of ascorbyl 2-monophosphate from aqueous alkaline reaction mixtures as are obtained on reaction of ascorbic acid with a molar excess of phosphorus oxychloride in the presence of a tertiary amine while maintaining a pH of from 12 to 13 during the reaction by means of an aqueous alkali metal hydroxide solution, which comprises a) starting from a reaction mixture which has been obtained by reacting ascorbic acid with phosphorus oxychloride in the presence of pyridine while maintaining a pH of from 12 to 13 by means of an aqueous potassium hydroxide solution, b) precipitating, as potassium magnesium phosphate, the phosphate ions which have been formed in this reaction by means of magnesium chloride in amounts of about 1 mol per mol of phosphate ions, c) removing the potassium magnesium phosphate, d) distilling the remaining aqueous solution to remove the pyridine together with part of the water, e) reacting the resulting aqueous solution with calcium chloride and f) isolating the calcium salt of ascorbyl 2-monophosphate which crystallizes thereby, or first distilling the pyridine-water mixture according to step (d) from the reaction mixture obtained in step (a) and thereafter carrying out steps (b), (c), (e) and (f).

5 Claims, No Drawings

PREPARATION OF CALCIUM L-ASCORBATE 2-PHOSPHATE

The present invention relates to a process for preparing the calcium salt of L-ascorbyl 2-monophosphate (also called calcium L-ascorbate 2-phosphate), which is an L-ascorbate 2-phosphate with very good industrial application properties.

L-Ascorbic acid (vitamin C) is an essential part of a balanced diet for humans and it is common to recommend dietetic administration of this vitamin. However, vitamin C is the least stable vitamin in foodstuffs because it reacts extremely readily with atmospheric oxygen. It is known that ascorbic acid can be made more stable to oxygen and heat by converting it into suitable derivatives. This is particularly important for the use, which has recently become widespread, of vitamin C in fish farming, for which the sparingly soluble calcium salt is particularly suitable.

Ascorbic acid monophosphate (AAMP) has the following considerable advantages compared with free ascorbic acid (AA):
1. relatively stable to oxidation,
2. general bioavailability because it can be cleaved by phosphatases in vivo and in vitro to ascorbic acid (this has been demonstrated, for example, in guinea pigs, broilers, piglets, rhesus monkeys and fish),
3. high thermal stability, and thus amenable to processing in extruders, and
4. very stable to hydrolysis.

The disadvantage of almost all known processes for preparing ascorbic acid monophosphate is that they are suitable only for the small scale because the described workup is much too elaborate for industrial implementation. The problem is that the required product must be separated from a large excess of inorganic salts derived from the phosphorylation process. Thus, for example, the reaction solution resulting from the phosphorylation process of U.S. Pat. No. 4,179,445 contains per equivalent of required product about 4.5 equivalents of KCl and 1.8 equivalents of $K_3PO_4$, ie. together about 6 equivalents of inorganic salts. The workup in this process involves the complete reaction mixture being passed through a column containing a strongly acid cation exchanger to remove salts, the eluate from the column being neutralized with $Mg(OH)_2$, and the resulting magnesium L-ascorbate 2-phosphate being precipitated with ethanol.

The workup of the phosphorylation mixture obtained in the process disclosed in U.S. Pat. No. 4,724,262 also requires the use of an ion exchanger (in this case a weakly basic anion exchanger), which would be too costly for industrial implementation.

The process disclosed in EP-A 426 020 requires removal of salts by a strongly acid cation exchanger in combination with purification with active carbon to isolate ascorbate 2-phosphate. The required product is finally obtained in this case as a magnesium salt by methanol precipitation.

The processes disclosed in DE-A 39 09 198 and DE-A 40 00 977 represented an advance compared with the prior art described, and they involved initially precipitating the excess phosphate as $KMgPO_4$ and then most of the KCl present in the solution with methanol before the solution was treated with an ion exchanger and/or the L-ascorbate 2-phosphate was precipitated as the potassium magnesium salt which crystallizes well.

In the process of DE-A 4 026 787, the excess phosphoric acid in the phosphorylation mixture is removed as $KMgPO_4$ by adding 2 mol of $MgCl_2$, part of the KCl is removed by crystallization, and finally the remaining KCl is removed by electrodialysis from the solution of the potassium magnesium salt. This process is not entirely satisfactory for industrial implementation either.

Two processes have been disclosed to date for the specific preparation of the Ca salt. In the process disclosed in U.S. Pat. No. 4,179,445 (or Carbohydrate Res. 67 (1978) 127), the calcium salt is prepared starting from the corresponding crystalline tricyclohexylammonium salt by removing salts on a strongly acid ion exchanger and subsequently adding $Ca(OH)_2$. The disadvantage of this process is the elaborate preparation of the precursor due to the use of an additional ion exchanger so that two salt-removal steps are necessary for the preparation of Ca AAMP.

The process disclosed in WO-A 91/13895 is more advantageous. In this case, the phosphorylation of ascorbic acid is carried out with "preformed" sodium dichlorophosphate in the presence of trimethylamine at pH 12 (pH control with 28% strength NaOH). Excess phosphate is precipitated as $Na_3PO_4$ during the reaction and is filtered off at $-8°$ C. Addition of the concentrated filtrate to an aqueous $CaCl_2$ solution results in crystalline Ca ascorbate 2-monophosphate. The disadvantages of this process are that complicated temperature and pH control are necessary for the reaction, the trimethylamine is difficult to recycle, the removal of the $Na_3PO_4$ has to be carried out at $-8°$ C., and the purity of the precipitated calcium salt is not sufficient for all purposes and makes further purification of the phosphates with the aid of certain crystallization bases necessary.

It is an object of the present invention to improve the workup of aqueous alkaline reaction mixtures as are obtained on reaction of ascorbic acid with excess $POCl_3$ in the presence of a tertiary amine while maintaining a pH of from 12 to 13 during the reaction to isolate calcium L-ascorbate 2-phosphate in such a way that it can also be carried out advantageously on the industrial scale.

We have found that this object is achieved by a process for isolating the calcium salt of ascorbyl 2-monosphophate of the formula I

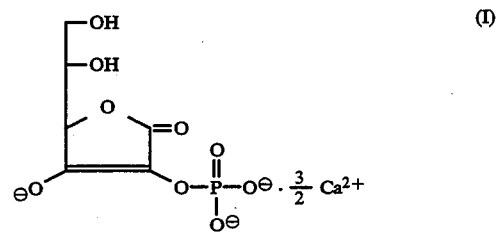

from aqueous alkaline reaction mixtures as are obtained on reaction of ascorbic acid with a molar excess of phosphorus oxychloride in the presence of a tertiary amine while maintaining a pH of from 12 to 13 during the reaction by means of an aqueous alkali metal hydroxide solution, which comprises a) starting from a reaction mixture which has been obtained by reacting ascorbic acid with phosphorus oxychloride in the presence of pyridine while maintaining a pH of from 12 to 13 by means of an aqueous potassium hydroxide solution, b) precipitating, as potassium magnesium phosphate, the phosphate ions which have been formed in this reaction by means of magnesium chloride in amounts of about 0.9–1.1, preferably about 1, mol per mol of phosphate ions, c) removing the potassium magnesium phosphate, d) distilling the remaining aqueous solution to remove the pyridine together with part of the water, e) reacting the resulting aqueous solution with calcium chloride and f) isolating the calcium salt I which crystallizes thereby, or first distilling the pyridine-water mixture according to step (d) from the reaction mixture obtained in step (a) and thereafter carrying out steps (b), (c), (e) and (f).

The process according to the invention is particularly advantageous when in step a) the ascorbic acid is reacted with about 2 mole equivalents of phosphorus oxychloride in the presence of about 4.5–5.5 mol of pyridine, and/or in step b) the phosphate ions are precipitated as potassium magnesium phosphate at from 0° to 30° C. and a pH of about 9.5, and/or in step e) about 1.5–1.9 mol of calcium chloride in the form of an aqueous solution are added to the aqueous solution, and/or in step e) an aqueous calcium chloride solution is added to the aqueous solution at a pH of from 7 to 10.

The starting compound used in the process according to the invention is n-ascorbic acid, ie. it is possible to dispense with the elaborate conversion into 5,6-O-isopropylideneascorbic acid.

The phosphorylation is essentially carried out under the conditions described in U.S. Pat. No. 4 179 445.

The phosphorylation takes place particularly advantageous when the ascorbic acid is employed in an initial concentration of about 0.15–0.6, preferably 0.2–0.4, mol per liter of reaction mixture. The amount of pyridine is advantageously about five times the molar amount of ascorbic acid.

Water is advantageously used as solvent. The phosphorus oxychloride is generally used in amounts of about 1.5–2.2, preferably 1.7–2.0, mol per mol of ascorbic acid.

Maintaining the pH in the reaction mixture during the phosphorylation is important for obtaining yields of economic interest. The aqueous potassium hydroxide solution used to control the pH can be from 20 to 70, preferably 30 to 60, % by weight.

After the $POCl_3$ addition is complete, the pH is expediently adjusted to 9–10, and the temperature is raised to room temperature (about 20° C.).

The magnesium chloride used to precipitate the phosphate ions formed during the phosphorylation is advantageously in the form of an aqueous solution.

The amount of $MgCl_2$ is generally about 0.9–1.1, preferably about 1, mol per mol of inorganic phosphate present in the reaction mixture. To complete the precipitation of the $KMgPO_4$, the mixture is stirred for about 1–4, preferably 1.5–3, hours after addition of the $MgCl_2$ solution. The pH of the mixture during this precipitation should expediently be about 8–10, preferably about 9.5.

The mother liquor after removal of the crystallized $KMgPO_4$ is distilled to remove the pyridine and part of the water.

To prepare, calcium ascorbate 2-phosphate, in general the resulting solution is slowly added dropwise to an aqueous $CaCl_2$ solution, and the resulting mixture is then stirred at a pH of about 9 and room temperature for about 10–24 hours.

A particularly advantageous embodiment of the process according to the invention comprises distilling the pyridine-water mixture after step (a) and then carrying out the remaining steps. In this case it is advisable to adjust the bottom product to a pH of about 7.5–11. The losses of pyridine can thus be minimized.

The process according to the invention can be used to prepare the calcium salt of ascorbyl 2-monophosphate, which is required for use as vitamin C in fish farming, in good yields and in adequate purity in a way which is simple to implement industrially.

EXAMPLE 1 a) Phosphorylation of ascorbic acid

A 2 l four-neck flask which is fitted with a two-neck adaptor and a three-neck adaptor and with a stirrer, a thermometer, a combination pH electrode (KCl filling), a KOH metering device (pH-control led Prominent Dulcometer), a $POCl_3$ metering device and a device for introducing $N_2$ was flushed with N2 and then 670.0 ml of water and 79.1 g (1 mol) of pyridine were introduced. The pH-controlled KOH metering pump was started with a set value of 13. The contents of the flask were cooled to 0° C. and, during the cooling, 35.2 g (0.2 mol) of ascorbic acid were introduced, with about 47 g of a 50% strength aqueous potassium hydroxide solution being used for the neutralization. Subsequently, while maintaining the mixture at pH 13 and at 0° C. by cooling, 36 ml (0.394 mol) $POCl_3$ were added at a rate of 0.3 ml/min. After the $POCl_3$ addition was complete, the pH set value was adjusted to 9.5, and the reaction mixture was warmed to 20° C.

b) Removal of excess phosphoric acid 63.5 ml of a 30% strength aqueous magnesium chloride solution (0.2 mol) were added over the course of 5 minutes (min) to the solution obtained in stage a) while maintaining a pH of 9.5, and the reaction mixture was then stirred at pH 9.5 for 2 hours (h).

The precipitated $KMgPO_4 \times 4-6H_2O$ was subsequently removed by filtration with suction and washed with $2\times 40$ ml of water. The mother liquor was concentrated to 600 g at 60° C. and 50 mbar, during which the pyridine was also removed from the mixture. It contained, according to HPLC, tripotassium-ascorbate 2-phosphate in a yield of 72–75% of theory.

c) Precipitation of ascorbic acid 2-monophosphate as calcium salt

The concentrated solution obtained in stage b) was added dropwise over the course of 60 min to 180 ml of a 2 molar aqueous $CaCl_2$ solution, and the mixture was then stirred at pH 9 and room temperature (RT) for 22 h. The crystals which had formed were filtered off with suction and washed with $5\times 50$ ml of water and then spread out and dried in a stream of nitrogen for 15 h and in an oven at 80° C. and 5 mbar for 24 h. 58 g of the required calcium L-ascorbate 2-phosphate were obtained (containing 42% by weight of ascorbic acid according to HPLC), corresponding to a yield of 69% of theory based on ascorbic acid.

The same result was achieved by distilling the pyridine-water mixture after step (a) with the bottom product adjusted to pH 10. The subsequently precipitated potassium magnesium phosphate was practically free from adsorbed pyridine.

EXAMPLE 2 a) 530 ml of water and 79.1 g (1 mol) of pyridine were introduced into the apparatus described in Example 1. The contents of the flask were cooled to 0° C. and, during the cooling and, while maintaining pH 13, 35.2 g (0.2 mol) of ascorbic acid were introduced, with about 47 g of a 50% strength aqueous KOH being used for the neutralization.. Subsequently, while maintaining pH 13 with 30% strength aqueous KOH and 0° C. by cooling, 36.0 ml (0.394 mol) of $POCl_3$ were added at a rate of 0.3 ml/min, and the reaction mixture was subsequently allowed to warm to 20 ° C.

b) 63.5 ml of a 30% strength aqueous $MgCl_2$ solution (0.2 mol) were added over the course of 5 min to the solution obtained in stage a) while maintaining a pH of 9.5 with 50% strength KOH, and the reaction mixture was then stirred at pH 9.5 for 2 h, the precipitated $KMgPO_4 \times 4-6H_2O$ was filtered off with suction and washed, and the mother liquor was distilled to remove the pyridine together with part of the water. In total, 47 g of a 50% strength and 350 g of a 30% strength aqueous KOH were used.

c) The concentrated solution obtained as in Example 2b) was worked up as in Example 1c). Calcium L-ascorbate 2-phosphate was obtained in a yield of 69.2% of theory.

We claim:

1. A process for isolating the calcium salt of ascorbyl 2-monophosphate of the formula I

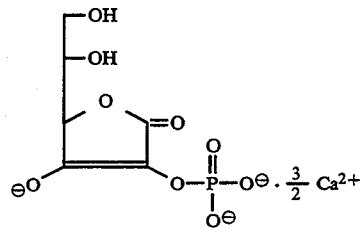

from aqueous alkaline reaction mixtures as are obtained on reaction of ascorbic acid with a molar excess of phosphorus oxychloride in the presence of a tertiary amine while maintaining a pH of from 12 to 13 during the reaction by means of an aqueous alkali metal hydroxide solution, which comprises
   a) starting from a reaction mixture which has been obtained by reacting ascorbic acid with phosphorus oxychloride in the presence of pyridine while maintaining a pH of from 12 to 13 by means of an aqueous potassium hydroxide solution,
   b) precipitating, as potassium magnesium phosphate, the phosphate ions which have been formed in this reaction by means of magnesium chloride in amounts of about 0.9–1.1 mol per mol of phosphate ions,
   c) removing the potassium magnesium phosphate,
   d) distilling the remaining aqueous solution to remove the pyridine together with part of the water,
   e) reacting the resulting aqueous solution with calcium chloride and
   f) isolating the calcium salt I which crystallizes thereby, or first distilling the pyridine-water mixture according to step (d) from the reaction mixture obtained in step (a) and thereafter carrying out steps (b), (c), (e) and (f).

2. The process of claim 1, wherein in step a) the ascorbic acid is reacted with about 2 mole equivalents of phosphorus oxychloride in the presence of about 4.5–5.5 mol of pyridine.

3. The process of claim 1, wherein in step b) the phosphate ions are precipitated as potassium magnesium phosphate at from 0° to 30° C. and at a pH of about 9.5.

4. The process of claim 1, wherein in step e) the aqueous solution is reacted with about 1.5–1.9 mol of calcium chloride in the form of an aqueous solution.

5. The process of claim 1, wherein in step e) an aqueous calcium chloride solution is added to the aqueous solution at a pH of from 7 to 10.

* * * * *